United States Patent
Utsui (10) Patent No.: US 6,936,004 B2
(45) Date of Patent: Aug. 30, 2005

(54) PROBE AND FLUORESCENT DIAGNOSTIC SYSTEM

(75) Inventor: Tetsuya Utsui, Tokyo (JP)

(73) Assignee: PENTAX Corporation, Tokyo (JP)

( * ) Notice: Subject to any disclaimer, the term of this patent is extended or adjusted under 35 U.S.C. 154(b) by 230 days.

(21) Appl. No.: 10/136,410

(22) Filed: May 2, 2002

(65) Prior Publication Data

US 2003/0045780 A1 Mar. 6, 2003

(30) Foreign Application Priority Data

Sep. 6, 2001 (JP) .......................... 2001-269853

(51) Int. Cl.$^7$ .......................... A61B 1/018; A61B 1/07; G02B 6/04
(52) U.S. Cl. .................... 600/182; 600/129; 600/478; 385/115
(58) Field of Search ................. 600/476, 478, 600/182, 114, 104, 128; 385/115, 116, 117

(56) References Cited

U.S. PATENT DOCUMENTS 4,648,892 A    3/1987  Kittrell et al.
4,669,467 A    6/1987  Willett et al.
4,718,417 A    1/1988  Kittrell et al.

FOREIGN PATENT DOCUMENTS

JP          2589674         11/1986

*Primary Examiner*—John P. Leubecker
(74) *Attorney, Agent, or Firm*—Greenblum & Bernstein, P.L.C.

(57) ABSTRACT

A probe, which includes a plurality of first optical fibers and a plurality of second optical fibers that are tied as a composite bundle at a distal end side with forming a center channel through which a treatment instrument can be drawn. The first optical fibers are tied as a first branch bundle at a proximal end side and the second optical fibers are tied as a second branch bundle that is separated form the first branch bundle at the proximal end side. With this construction, a treatment instrument is available even if the probe is drawn through a forceps channel of an endoscope because the treatment instrument can be drawn through the center channel formed in the composite bundle.

20 Claims, 8 Drawing Sheets

PROBE AND FLUORESCENT DIAGNOSTIC SYSTEM

BACKGROUND OF THE INVENTION

The present invention relates to a probe employed in an endoscope system and a fluorescent diagnostic system employing the probe.

When tissue of a living body is illuminated with UV light, the tissue is excited and generates fluorescence (autofluorescence). The fluorescence from tissue that is suffering from a lesion such as a tumor has different characteristics from the fluorescence from normal tissue. Concretely, while the fluorescence from normal tissue has larger intensity in green range than that in red range, the difference between intensities in a green range and a red range is relatively small in the fluorescence from tissue suffering from a lesion. A fluorescence diagnostic system that determines the presence or absence of a lesion in tissue of a living body by comparing the intensity in the green range and the intensity in the red range of autofluorescence through the use of the above described characteristics has been developed.

The fluorescence diagnostic system is provided with a probe that illuminates a living body with excitation light and guides light from the living body. The probe consists of a plurality of illumination optical fibers that guide excitation light and a plurality of detection optical fibers that guide fluorescence. The illumination optical fibers and the detection optical fibers are tied as a composite bundle at the distal end side and are separately tied as an illumination bundle consisting of the illumination optical fibers and a detection bundle consisting of the detection optical fibers at the proximal end side. Further, the fluorescence diagnostic system includes an excitation light source that emits illumination light to be incident on the proximal end of the illumination bundle and a detecting unit that is connected with the proximal end of the detection bundle to receive light from a living body.

In general, the probe is drawn through a forceps channel of an endoscope during observation. That is, an operator directs the distal end of the endoscope toward tissue to be examined with jutting the probe from the distal end of the endoscope. Excitation light guided through the illumination bundle emerges from the distal end of the probe toward the tissue. Then, the tissue illuminated by the excitation light generates autofluorescence. This autofluorescence and the excitation light reflected by the surface of the tissue are incident on the distal end of the probe. Detection light incident on the detection bundle is transmitted by the optical fibers of the detection bundle and emerges from the proximal end of the detection bundle to be detected by the detecting unit. The detecting unit displays the intensity in the green range and the intensity in the red range of the detection light on a monitor. The operator judges that the tissue under examination is normal when the difference between the intensities is large and that the tissue under examination is suffering from a lesion when the difference between the intensities is small.

However, according to the above described diagnostic system, since the probe fills one forceps channel of the endoscope, the forceps channel is unavailable during fluorescence diagnosis when the endoscope has one forceps channel.

Further, when the operator judged that the tissue under examination is suffering from a lesion as a result of the fluorescence diagnosis, the operator often treat the tissue with various treatment instruments such as a forceps or a laser probe. However, if the forceps channel is occupied with the probe, the operator must pull out the probe as a first step and then insert a treatment instrument into the forceps channel. Such a replacement requires much expense in time and effort. Further, the direction of the distal end of the endoscope directed to the tissue suffering from a lesion may deviate during the replacement, which requires time to redirect the distal end toward the tissue suffering from a lesion.

SUMMARY OF THE INVENTION

It is therefore an object of the present invention to provide a probe that does not occupy a forceps channel even if the probe is drawn through the forceps channel and a fluorescence diagnostic system including such a probe.

For the above object, according to the present invention, there is provided an improved probe, which includes a plurality of first optical fibers and a plurality of second optical fibers that are tied as a composite bundle at a distal end side with forming a center channel through which a treatment instrument can be drawn. The first optical fibers are tied as a first branch bundle at a proximal end side and the second optical fibers are tied as a second branch bundle that is separated form the first branch bundle at the proximal end side.

The distal end corresponds to a tip end of an insertion portion of an endoscope and the proximal end corresponds to a side of a control unit of the endoscope.

With this construction, a treatment instrument is available even if the probe is drawn through a forceps channel of an endoscope because the treatment instrument can be drawn through the center channel formed in the composite bundle.

The probe of the invention is available for a fluorescent diagnostic system. The fluorescent diagnostic system further includes an excitation light source unit that emits excitation light and a detection unit that detects the light from a tissue of a living body. The excitation light is guided through the first optical fibers to excite the tissue so as to generate autofluorescence and the light from the tissue is guided through the second optical fibers. Various treatments are available during fluorescent diagnosis without replacing the probe with a treatment instrument.

A plurality of third optical fibers may be drawn through the center channel of the composite bundle. In such a case, the third optical fibers are tied as a third branch bundle that is separated from the first and second branch bundles. The third optical fibers may be used to guide a therapeutic laser beam emitted from a laser therapeutic unit to treat the tissue.

Further, the cross-sectional area of the first optical fibers may be larger than that of the second optical fibers. When the diameters of first and second optical fibers are identical, a number of the first optical fibers may be larger than that of the second optical fibers. Further, a diameter of each of the first optical fibers may be larger than a diameter of each of the second optical fibers.

DESCRIPTION OF THE EMBODIMENTS

Embodiments of the present invention will be described hereinafter with reference to the drawings.

First Embodiment

Figure 1:
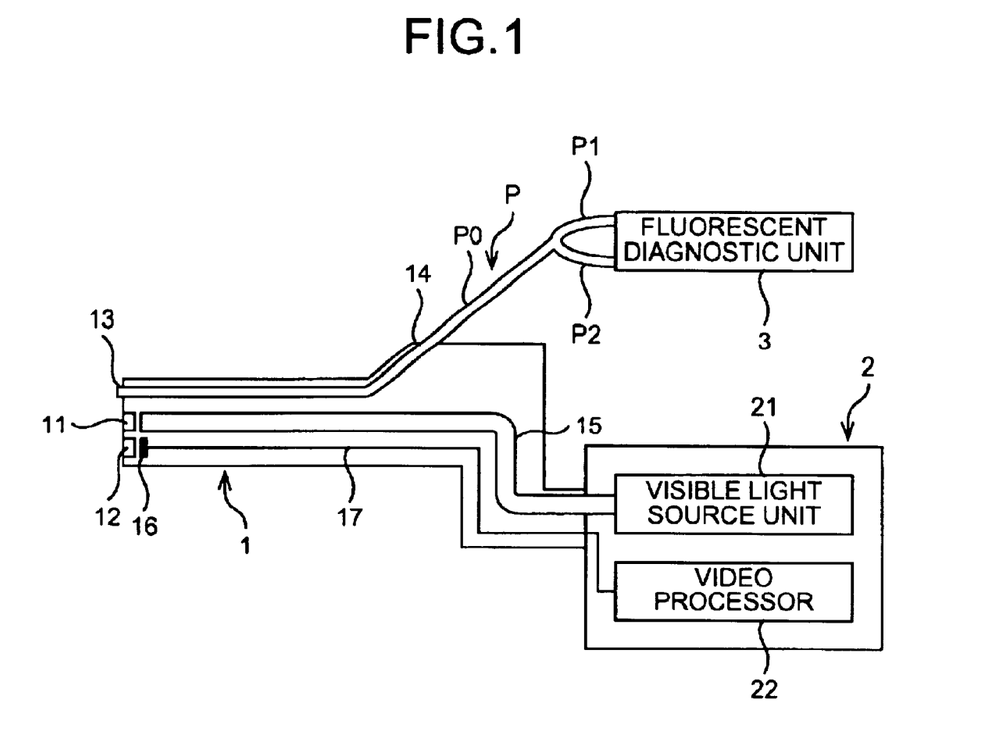
FIG. 1 is a schematic block diagram of an endoscope system employing a probe according to a first embodiment.

FIG. 1 is a schematic block diagram of an endoscope system employing a probe according to a first embodiment. The endoscope system is provided with an electronic endoscope 1, a light source/processor unit 2, a probe P and a fluorescent diagnostic unit 3.

The electronic endoscope 1 has an insertion portion that can be inserted into a living body and an operation unit that is connected to a proximal end of the insertion portion. The insertion portion is formed as a flexible tube. A bending portion is installed at a distal end of the insertion portion and a tip portion made of hard material is fixed at the tip end of the bending portion. Various kinds of dials and switches are arranged on the operation unit.

There are at least three through holes in the tip portion of the endoscope 1. At the distal ends of a pair of through holes, a distribution lens 11 and an object lens 12 are attached, respectively. The other through hole is used as a forceps hole 13. A capillary that connects the forceps hole 13 to an opening formed on the operation unit (a forceps hole 14 at the proximal end side) is drawn through inside the endoscope 1, and the capillary is used as a forceps channel.

Further, the endoscope 1 has a light guide fiber bundle 15 that consists of a plurality of optical fibers tied to each other. The light guide fiber bundle 15 is drawn through the endoscope 1 and the distal end thereof faces the distribution lens 11. The proximal end of the light guide fiber bundle 15 is drawn into the light source/processor unit 2.

At the tip portion of the endoscope 1, an image sensor 16, which is a CCD area sensor, is arranged. The image-taking surface of the image sensor 16 is located near the conjugate point of tissue under examination through the object lens 12 when the tip portion of the endoscope 1 faces the tissue. The image sensor 16 gets the image data of the tissue and outputs the image data to a video processor 22 via a data line 17. Although it is not shown in FIG. 1, a filter that intercepts the ultraviolet light and permits transmission of the visible light may be located in the optical path between the object lens 12 and the image sensor 16.

The light source/processor unit 2 is provided with a visible light source unit 21 that emits visible light and the video processor 22 that is connected with the image sensor 16 with the data line 17. The visible light source unit 21 sequentially emits blue light (B-light), green light (G-light) and red light (R-light) over and over. The B-, G- and R-lights that are incident on the proximal end of the light guide fiber bundle 15 are transmitted through the light guide fiber bundle 15 and diffused by the distribution lens 11 to illuminate the tissue opposite to the distal end of the endoscope 1. Images of the tissue formed by the B-, G- and R-lights are sequentially formed on the image-taking surface of the image sensor 16. The image sensor 16 converts these images into the respective image data and transmits them to the video processor 22 via the data line 17.

The video processor 22 composes the image data of the B-, G- and R-lights to produce a color image of the tissue by a plane sequence method. The video processor 22 displays the color image on a monitor (not shown). An operator observes the color image of the tissue displayed on the monitor.

Figure 2:
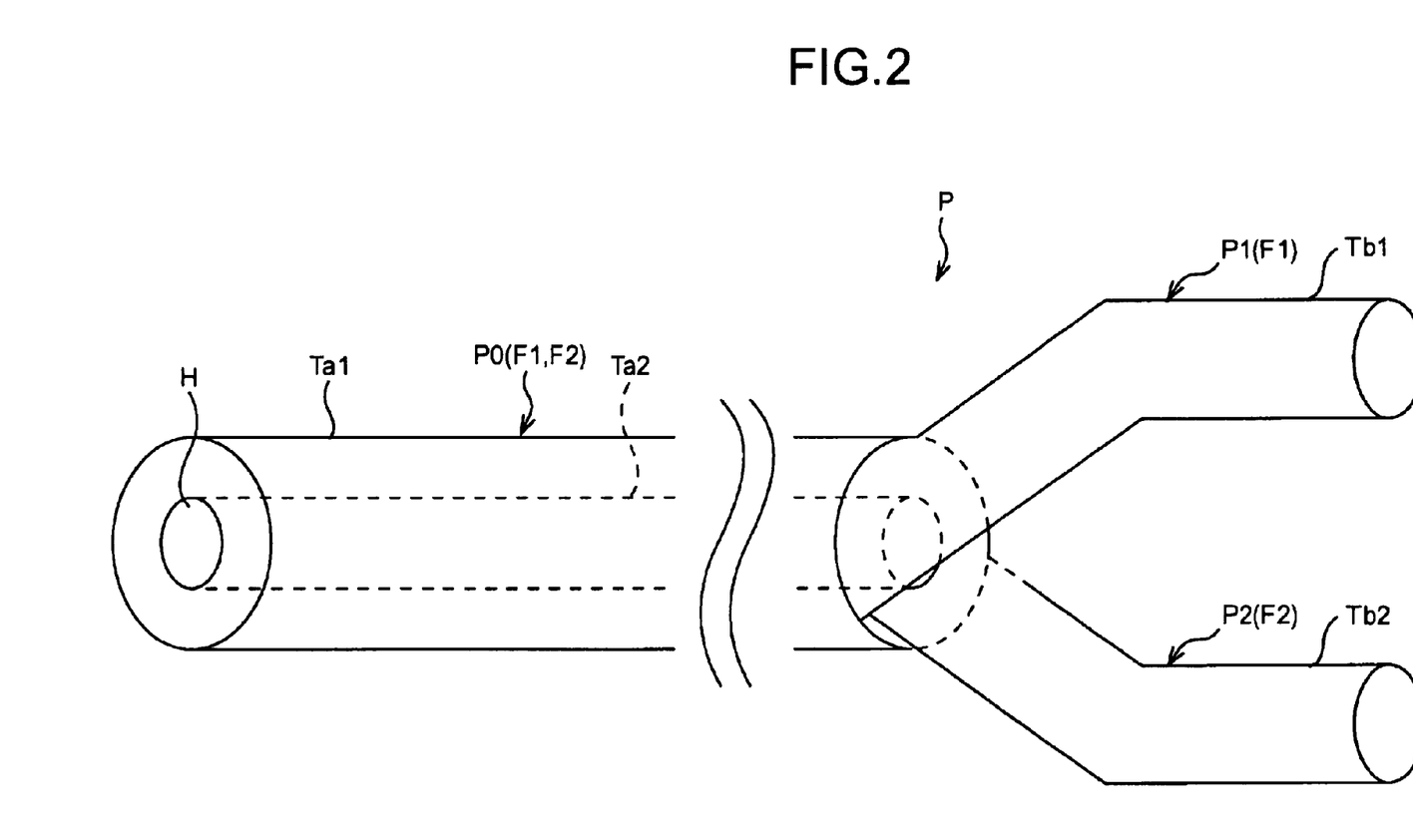
FIG. 2 is a schematic view of the probe according to the first embodiment.

FIG. 2 is a schematic view of the probe P. The probe P includes a plurality of first optical fibers F1 and a plurality of second optical fibers F2. The first and second optical fibers F1 and F2 are tied as a composite bundle P0 at a distal end side with forming a center channel that has an opening H at the distal end.

Figure 3:
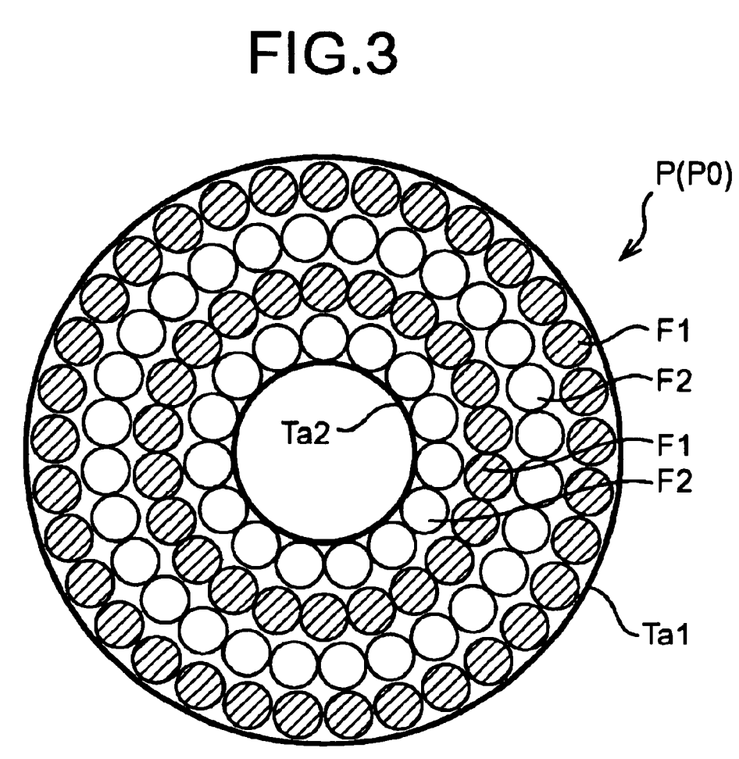
FIG. 3 is a cross-sectional view of a composite bundle of the probe according to the first embodiment.

As shown in FIG. 3, which is a cross-sectional view of the composite bundle P0 of the probe P, the first and second optical fibers F1 and F2 are arranged to form alternative circular layers. The outer surface of the composite bundle P0 is covered with an outer tube Ta1 and the inner surface thereof is covered with an inner tube Ta2. In the other words, the first and second optical fibers F1 and F2 fill the space between the outer and inner tubes Ta1 and Ta2. The outer diameter of the composite bundle P0 is determined such that the composite bundle P0 can be drawn through the forceps channel of the endoscope 1. Further, the inner diameter of the composite bundle P0 is determined such that a treatment instrument such as a forceps for an endoscope, a laser probe or a snare can be drawn therethrough.

As shown in FIG. 2, the first optical fibers F1 are tied as a first branch bundle P1 at a proximal end side and the second optical fibers F2 are tied as a second branch bundle P2 that is separated form the first branch bundle P1 at the proximal end side. The first branch bundle P1 is covered with a first branch tube Tb1 and the second branch bundle P2 is covered with a second branch tube Tb2. Since the tubes are flexible, the probe P is flexible along its entire length.

Figure 4:
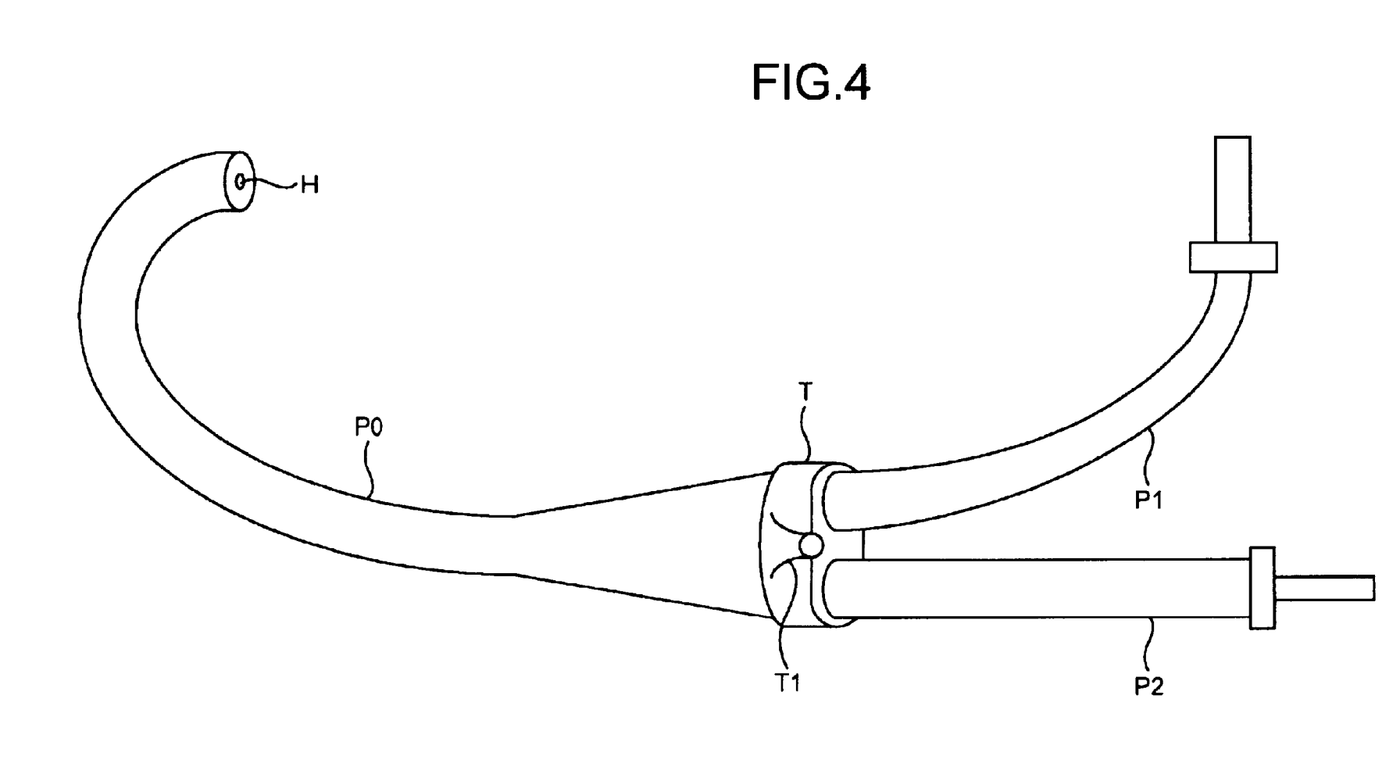
FIG. 4 is an external view of the probe according to the first embodiment.

FIG. 4 is an external view of the probe P. The probe P further includes a connection member T having a shape of an elliptic cylinder. The composite bundle P0 is connected to the connection member T at one side and the first and second branch bundles P1 and P2 are connected to the other side of the connection member T. That is, the connection member T is located at a branch point of the first and second branch bundles. The connection member T has a projected opening T1 that is connected to the opening H of the distal end through the inner tube Ta2

Figure 5:
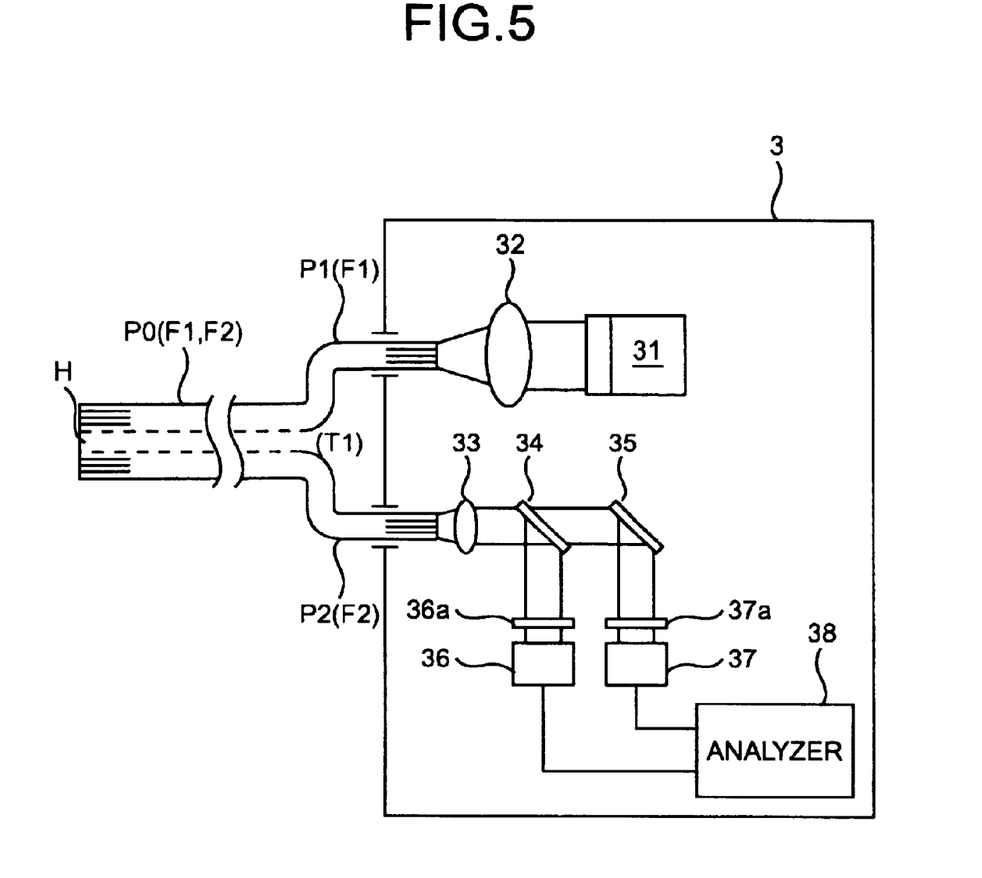
FIG. 5 is a schematic block diagram of a fluorescent diagnostic system according to the first embodiment.

FIG. 5 is a schematic block diagram of the fluorescent diagnostic unit 3 that includes an excitation light source 31 and a condenser lens 32. The excitation light source 31 emits excitation light (ultraviolet light) as a parallel beam. The condenser lens 32 is located in an optical path of the excitation light and converges the excitation light onto the proximal end of the first optical fibers F1 of the first fiber bundle P1. The excitation light is guided through the first optical fibers F1 and emerges from the distal end of the first optical fibers F1. When the tip portion of the endoscope 1 faces tissue of a living body, the excitation light illuminates the tissue. A part of the excitation light is absorbed by the tissue and the tissue generates autofluorescence. The remaining part of the excitation light is reflected by the tissue.

The autofluorescence and the reflected excitation light incident on the distal end of the second optical fibers F2 are guided to the fluorescent diagnostic unit 3 and emerge from the proximal end of the second optical fibers F2.

The fluorescent diagnostic unit 3 further includes a collimator lens 33, a beam splitter 34, a mirror 35, a first detector 36, a second detector 37 and an analyzer 38. The light emerged from the proximal end of the second optical fibers F2 is converted into the parallel beam by the collimator lens 33 and is divided into two portions by the beam splitter 34.

The light reflected by the beam splitter 34 is incident on the first detector 36 via a green filter 36a that allows transmission of a green band with high efficiency while rejects out-of-band energy. The excitation light is removed by the green filter 36a. Therefore, the first detector 36 receives the green component of the autofluorescence and outputs an electric signal that represents the intensity of the green component in the autofluorescence.

On the other hand, the light passing through the beam splitter 34 is reflected by the mirror 35 and is incident on the second detector 37 via a red filter 37a that allows transmission of a red band with high efficiency while rejects out-of-band energy. The excitation light is removed by the green filter 36a. Therefore, the second detector 37 receives the red component of the autofluorescence and outputs an electric signal that represents the intensity of the red component in the autofluorescence.

The analyzer 38 is connected to both of the first and second detectors 36 and 37. The analyzer 38 gets the electric signals from the detectors and displays numerical data of the intensities of the signals and graphs drafted based on the numerical data.

As shown in FIG. 3, the cross-sectional area of the first optical fibers F1 is larger than that of the second optical fibers F2 because the number of the first optical fibers F1 is larger than a number of the second optical fibers F2 and the diameter of each first optical fiber F1 is identical to the diameter of each second optical fiber F2.

In order to increase the accuracy of the fluorescent diagnosis, it is preferable to increase the intensity of autofluorescent, which requires to increase the intensity of the excitation light. To satisfy the requirement in the limited total cross-sectional area, the cross-sectional area of the first optical fibers F1 should be larger than that of the second optical fibers F2.

With this construction of the first embodiment, the cross-sectional area of the first optical fibers F1 is larger than that of the second optical fibers F2, which keeps the intensities of the excitation light and autofluorescence high, assuring the accuracy of the fluorescent diagnosis.

Operations of the endoscope 1 according to the first embodiment will be described hereinafter. An operator inserts the insertion portion of the endoscope 1 into a living body and directs the tip portion thereof toward an tissue under observation. A color image of the tissue is displayed on the monitor. The operator observes the condition in the living body by looking the monitor.

Further, the operator observes the portion of the tissue selected through the color image observation with the fluorescent diagnostic unit 3 (fluorescent observation). That is, the operator inserts the probe P into the forceps channel from the forceps hole 14 at the proximal end side such that the distal end of the probe P juts from the forceps hole 13 at the distal end of the endoscope 1. Under this condition, the excitation light emerges from the distal end of the first optical fibers F1 of the probe P. The tissue illuminated by the excitation light generates autofluorescence. This autofluorescence and the excitation light reflected by the surface of the tissue are incident on the distal end of the probe P as detection light. The detection light incident on the second optical fibers F2 is guided to the fluorescent diagnostic unit 3 through the second branched bundle P2. And then, the analyzer 38 displays the intensities of the green component and the red component included in the detection light.

The operator judges that the tissue under examination is normal when the difference between the intensities is large and that the tissue under examination is suffering from a lesion when the difference between the intensities is small.

When the operator judges that the tissue is suffering from a lesion, the operator treats the tissue with a treatment instrument such as a forceps for an endoscope, a laser probe or a snare. During the treatment, the operator keeps the endoscope at the same position as in the observation and inserts the treatment instrument from the projected opening T1. The treatment instrument is drawn through the inner tube Ta2 and juts from the opening H at the tip portion of the probe P. Since the region faced to the tip end of the probe P is a target region of the treatment, the operator easily and accurately guides the treatment instrument to the target region.

Second Embodiment

Figure 6:
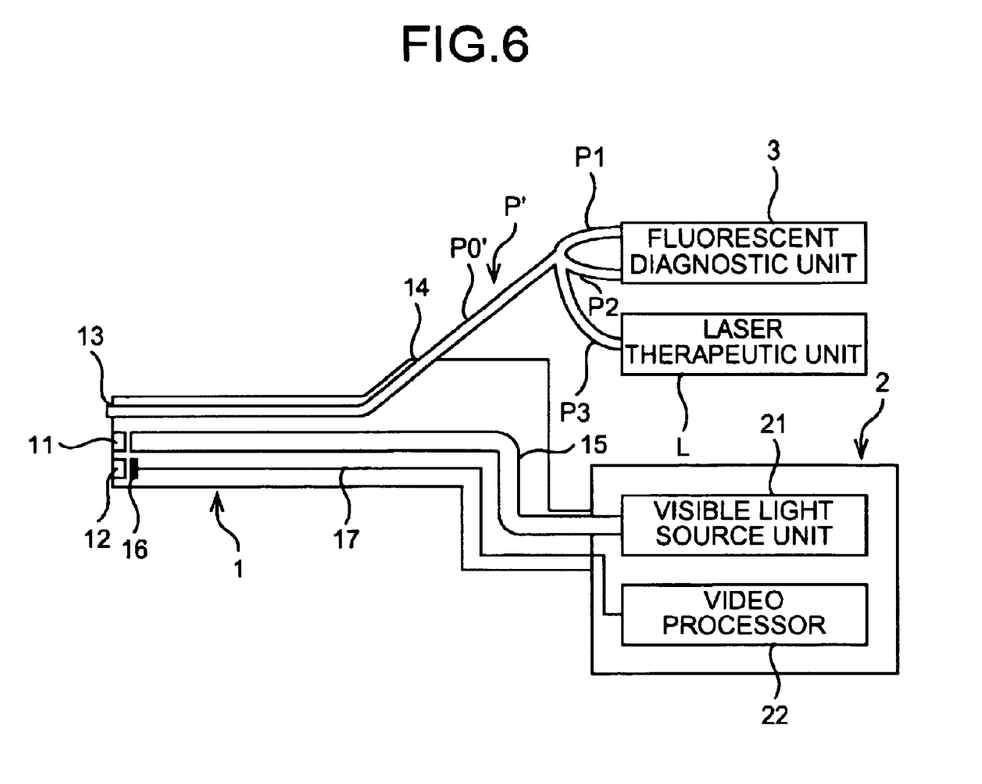
FIG. 6 is a schematic block diagram of an endoscope system employing a probe according to a second embodiment.

FIG. 6 is a schematic block diagram of an endoscope system employing a probe P' according to a second embodiment. Differences of the second embodiment from the first embodiment are that a probe P' has three optical fiber systems and a laser therapeutic unit L is provided.

Figure 7:
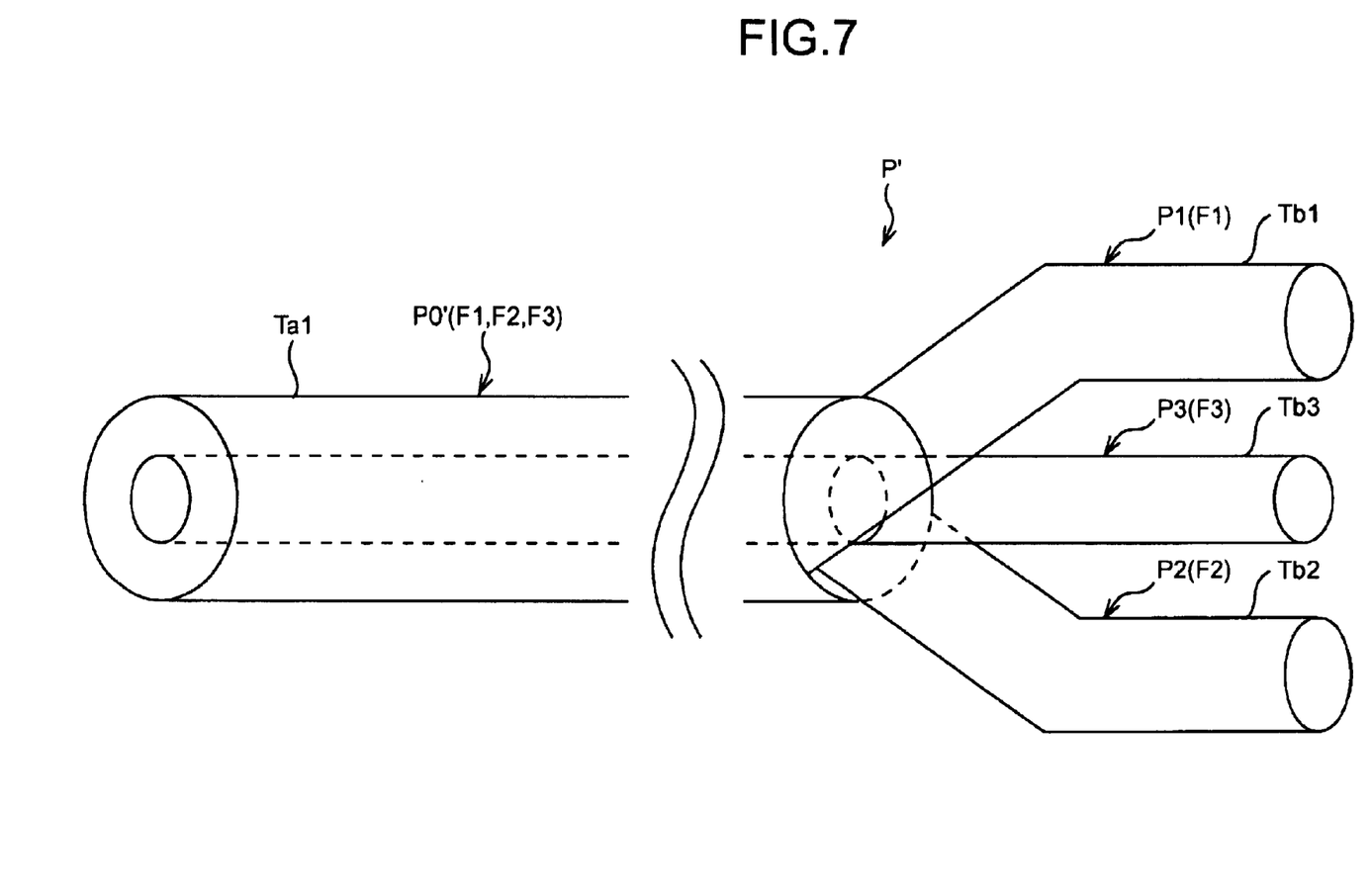
FIG. 7 is a schematic view of the probe according to the second embodiment.

FIG. 7 is a schematic view of the probe P'. The probe P' includes a plurality of first optical fibers F1 to guide the excitation light, a plurality of second optical fibers F2 to guide the detection light and a plurality of third optical fibers F3 to guide the therapeutic laser. The first, second and third optical fibers are tied as a composite bundle P0' at the distal end side and are covered by a tube Ta1.

Figure 8:
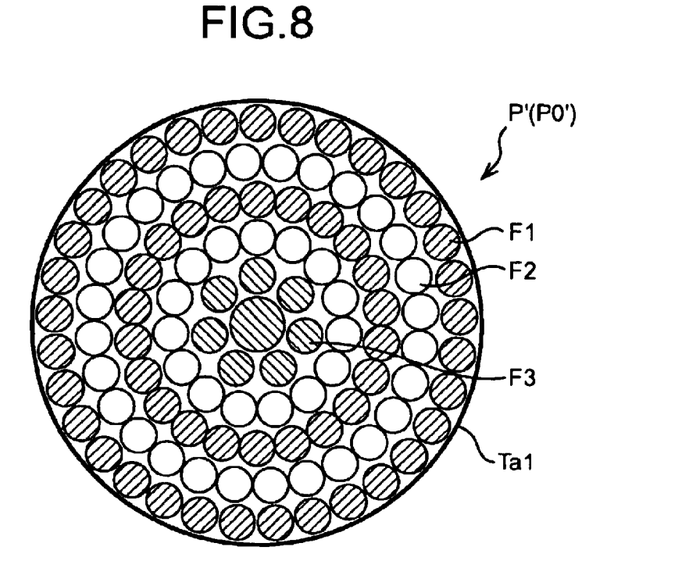
FIG. 8 is a cross-sectional view of a composite bundle of the probe according to the second embodiment.

FIG. 8 is a cross-sectional view of the composite bundle P0'. The tube Ta1 is flexible and the outer diameter of the composite bundle P0' is determined such that the composite bundle P0' can be drawn through the forceps channel of the endoscope 1. The first and second optical fibers F1 and F2 are arranged to form alternative circular layers as with the first embodiment and the third optical fibers F3 are arranged at the center of the composite bundle P0'. That is, the composite bundle P0' of the second embodiment is formed by inserting the third optical fibers F3 into the center channel of the composite bundle P0 of the first embodiment.

As shown in FIG. 7, the first optical fibers F1 are tied as a first branch bundle P1 at a proximal end side, the second optical fibers F2 are tied as a second branch bundle P2 and the third optical fibers F3 are tied as a third branch bundle P3. The first, second and third branch bundles P1, P2 and P3 are separated form each other and they are covered by tubes Tb1, Tb2 and Tb3, respectively.

As shown in FIG. 6, the first and second branch bundles P1 and P2 are connected to the fluorescent diagnostic unit 3 as with the first embodiment, while the third branch bundle P3 is connected to the laser therapeutic unit L. The laser therapeutic unit L is provided with a high-power laser source and converges the laser beam emitted from the high-power laser source onto the proximal end surface of the third branch bundle P3 to be incident on the third optical fibers F3. The incident laser beam is guided through the third optical fibers F3 and emerges from the tip end of the probe P'.

Accordingly, the operator can observe the tissue with the fluorescent diagnostic unit 3 in the same manner as the first embodiment. When the operator judges that the tissue is suffering from a lesion, the operator can operate the laser therapeutic unit to irradiate the tissue with the therapeutic laser beam. Since the region faced to the tip end of the probe P is a target region of the treatment, the operator easily and accurately guides the treatment instrument to the target region.

Third Embodiment

Figure 9:
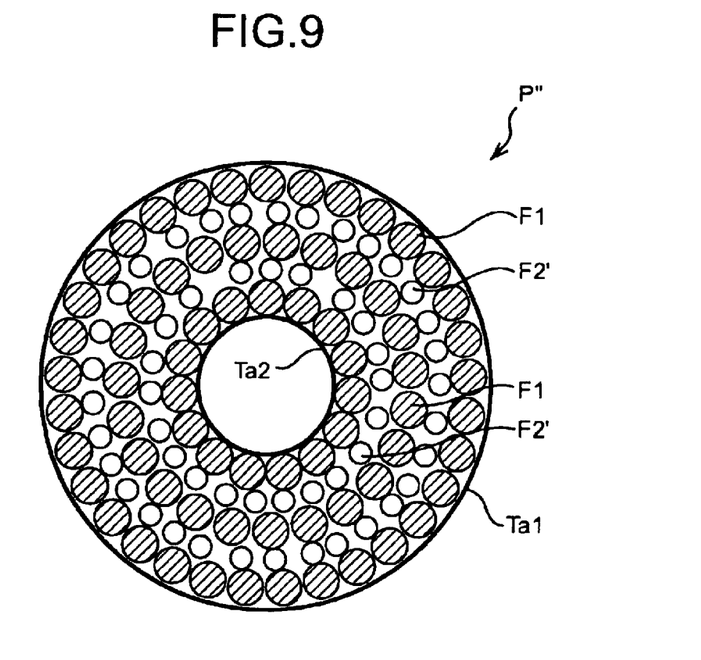
FIG. 9 is a cross-sectional view of a composite bundle of the probe according to a third embodiment.

FIG. 9 is a cross-sectional view of a composite bundle of a probe P'' according to a third embodiment. The basic construction of the third embodiment is identical with the first embodiment. That is, the probe P'' includes a plurality of first optical fibers F1 and a plurality of second optical fibers F2' that are tied to form the composite bundle as shown in FIG. 9 at the distal end side, and the first optical fibers F1 are tied as a first branch bundle at the proximal end side and the second optical fibers F2' are tied as a second branch bundle that is separated from the first branch bundle. The outer surface of the composite bundle is covered with an outer tube Ta1 and the inner surface thereof is covered with an inner tube Ta2.

However, the ratio of the cross-sectional area of the first optical fibers F1 to the total cross-sectional area is larger than that of the first embodiment. As compared with the first embodiment (FIG. 3), the diameter of each first optical fiber F1 is not changed, while the diameter of each second optical fiber F2' is smaller and the number of the first optical fibers F1 increases.

With this construction of the third embodiment, the cross-sectional area of the first optical fibers F1 becomes larger than that of the first embodiment, which increases the intensity of the excitation light, increasing the intensity of the autofluorescence. This enables more accurate fluorescent diagnosis.

The present disclosure relates to the subject matter contained in Japanese Patent Application No. 2001-269853, filed on Sep. 6, 2001, which are expressly incorporated herein by reference in its entirety.

What is claimed is:

1. A fluorescent diagnostic system comprising:
a probe that comprises:
a plurality of first optical fibers;
a plurality of second optical fibers, a cross-sectional area of said first optical fibers being larger than a cross-sectional area of said second optical fibers,
wherein said first and second optical fibers are tied as a composite bundle at a distal end side to provide a center channel configured to define an opening through which a treatment instrument can be moved, said first optical fibers are tied as a first branch bundle at a proximal end side and said second optical fibers are tied as a second branch bundle that is separated from said first branch bundle at the proximal end side;
an excitation light source unit that emits excitation light, said excitation light being guided through said first optical fibers to excite a tissue of a living body so as to generate autofluorescence; and
a detection unit that detects the light from the tissue guided through said second optical fibers.

2. The fluorescent diagnostic system according to claim 1, wherein a number of said first optical fibers is larger than a number of said second optical fibers.

3. The fluorescent diagnostic system according to claim 1, wherein a diameter of each of said first optical fibers is larger than a diameter of each of said second optical fibers.

4. The fluorescent diagnostic system according to claim 1, wherein the first and second optical fibers are configured as alternate circular layers.

5. The fluorescent diagnostic system according to claim 1, wherein each optical fiber of said fluorescent diagnostic system is one of either said plurality of first optical fibers or said plurality of second optical fibers.

6. The fluorescent diagnostic system according to claim 1, wherein said center channel defines an opening configured to receive a treatment tool insertable into a human body through the center channel.

7. A fluorescent diagnostic system comprising:
a probe that comprises:
a plurality of first optical fibers;
a plurality of second optical fibers, a cross-sectional area of said first optical fibers being larger than a cross-sectional area of said second optical fibers;
a plurality of third optical fibers,
wherein said first, second and third optical fibers are tied as a composite bundle at a distal end side, said first optical fibers are tied as a first branch bundle at a proximal end side, said second optical fibers are tied as a second branch bundle and said third optical fibers are tied as a third branch bundle, wherein said first, second and third branch bundles are separated from each other;
an excitation light source unit that emits excitation light, said excitation light being guided through said first optical fibers to excite a tissue of a living body so as to generate autofluorescence;
a detection unit that detects the light from the tissue guided through said second optical fibers; and
a laser therapeutic unit that emits a therapeutic laser beam, said therapeutic laser beam being guided through said third optical fibers to treat said tissue.

8. The fluorescent diagnostic system according to claim 7, wherein a number of said first optical fibers is larger than a number of said second optical fibers.

9. The fluorescent diagnostic system according to claim 7, wherein a diameter of each of said first optical fibers is larger than a diameter of each of said second optical fibers.

10. A probe comprising:
a plurality of first optical fibers; and
a plurality of second optical fibers,
wherein said first and second optical fibers are tied as a composite bundle at a distal end side to form a center channel through which a treatment instrument can be moved, said first optical fibers are tied as a first branch bundle at a proximal end side and said second optical fibers are tied as a second branch bundle that is separated from said first branch bundle at the proximal end side,
wherein each group of said first and second optical fibers forms a plurality of circular layers and the layers of said first optical fibers and the layers of said second optical fibers are alternatively arranged.

11. The probe according to claim 10, a cross-sectional area of said first optical fibers being larger than a cross-sectional area of said second optical fibers.

12. The probe according to claim 10, wherein a number of said first optical fibers is larger than a number of said second optical fibers.

13. The probe according to claim 10, wherein a diameter of each of said first optical fibers is larger than a diameter of each of said second optical fibers.

14. A probe comprising:
a plurality of first optical fibers;
a plurality of second optical fibers; and
a plurality of third optical fibers,
wherein said first, second and third optical fibers are tied as a composite bundle at a distal end side, said first optical fibers are tied as a first branch bundle at a proximal end side, said second optical fibers are tied as a second branch bundle and said third optical fibers are tied as a third branch bundle, wherein said first, second and third branch bundles are separated form each other;

wherein each group of said first and second optical fibers forms a plurality of circular layers and the layers of said first optical fibers and the layers of said second optical fibers are alternatively arranged.

15. The fluorescent diagnostic system according to claim 14, a cross-sectional area of said first optical fibers being larger than a cross-sectional area of said second optical fibers.

16. A fluorescent diagnostic system comprising:

a probe that comprises:

a plurality of first optical fibers; and a plurality of second optical fibers, an excitation light source unit that emits excitation light, said excitation light being guided through said first optical fibers to excite a tissue of a living body so as to generate autofluorescence; and a detection unit that detects the light from the tissue guided through said second optical fibers, wherein said first and second optical fibers are tied as a composite bundle at a distal end side to form a center channel through which a treatment instrument can be moved, said first optical fibers are tied as a first branch bundle at a proximal end side and said second optical fibers are tied as a second branch bundle that is separated from said first branch bundle at the proximal end side, and wherein each group of said first and second optical fibers forms a plurality of circular layers and the layers of said first optical fibers and the layers of said second optical fibers are alternatively arranged.

17. The fluorescent diagnostic system according to claim 16, a cross-sectional area of said first optical fibers being larger than a cross-sectional area of said second optical fibers.

18. A fluorescent diagnostic system comprising:

a probe that comprises:

a plurality of first optical fibers;

a plurality of second optical fibers;

a plurality of third optical fibers, an excitation light source unit that emits excitation light, said excitation light being guided through said first optical fibers to excite a tissue of a living body so as to generate autofluorescence;

a detection unit that detects the light from the tissue guided through said second optical fibers; and a laser therapeutic unit that emits a therapeutic laser beam, said therapeutic laser beam being guided through said third optical fibers to treat said tissue, wherein said first, second and third optical fibers are tied as a composite bundle at a distal end side, said first optical fibers are tied as a first branch bundle at a proximal end side, said second optical fibers are tied as a second branch bundle and said third optical fibers are tied as a third branch bundle, wherein said first, second and third branch bundles are separated from each other, and wherein each group of said first and second optical fibers forms a plurality of circular layers and the layers of said first optical fibers and the layers of said second optical fibers are alternatively arranged.

19. The fluorescent diagnostic system according to claim 18, a cross-sectional area of said first optical fibers being larger than a cross-sectional area of said second optical fibers.

20. A fluorescent diagnostic system comprising:

a probe that comprises:

a plurality of first optical fibers;

a plurality of second optical fibers, a cross-sectional area of said first optical fibers being larger than a cross-sectional area of said second optical fibers, wherein said first and second optical fibers are tied as a composite bundle at a distal end side to provide a center channel through which a treatment instrument can be moved, said first optical fibers are tied as a first branch bundle at a proximal end side and said second optical fibers are tied as a second branch bundle that is separated from said first branch bundle at the proximal end side;

an excitation light source unit that emits excitation light, said excitation light being guided through said first optical fibers to excite a tissue of a living body so as to generate autofluorescence; and a detection unit that detects the light from the tissue guided through said second optical fibers, wherein a diameter of each of said first optical fibers is larger than a diameter of each of said second optical fibers.

* * * * *